US009937331B2

(12) United States Patent
Burton et al.

(10) Patent No.: US 9,937,331 B2
(45) Date of Patent: Apr. 10, 2018

(54) INTEGRAL DILATION ELEMENT FOR A BALLOON CATHETER

(71) Applicant: Cook Medical Technologies LLC, Bloomington, IN (US)

(72) Inventors: David G. Burton, Bloomington, IN (US); Thomas Lysgaard, Solrod Strand (DK); Steen Aggerholm, St. Heddinge (DK); Per Elgaard, Haslev (DK); Kjeld Hjort, Holmegaard (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 267 days.

(21) Appl. No.: 15/043,002

(22) Filed: Feb. 12, 2016

(65) Prior Publication Data
US 2016/0158508 A1 Jun. 9, 2016

Related U.S. Application Data

(63) Continuation of application No. 13/690,507, filed on Nov. 30, 2012, now Pat. No. 9,302,079.

(60) Provisional application No. 61/566,232, filed on Dec. 2, 2011.

(51) Int. Cl.
A61M 29/00 (2006.01)
A61M 25/10 (2013.01)

(52) U.S. Cl.
CPC .... *A61M 25/1029* (2013.01); *A61M 25/1002* (2013.01); *A61M 25/104* (2013.01); *A61M 25/1034* (2013.01); *A61M 2025/1031* (2013.01); *A61M 2025/1086* (2013.01)

(58) Field of Classification Search
CPC .............. A61M 25/10; A61M 25/1002; A61M 25/104; A61M 25/1029; A61M 25/1034; A61M 2025/1031; A61M 2025/1086
See application file for complete search history.

(56) References Cited

U.S. PATENT DOCUMENTS

| 5,196,024 | A | 3/1993 | Barath |
| 5,569,272 | A | 10/1996 | Reed et al. |
| 6,358,266 | B1 | 3/2002 | Bonutti |
| 6,730,105 | B2 | 5/2004 | Shiber |
| 7,270,673 | B2 | 9/2007 | Yee et al. |
| 7,291,158 | B2 | 11/2007 | Crow et al. |
| 7,413,558 | B2 | 8/2008 | Kelley et al. |
| 7,494,497 | B2 * | 2/2009 | Weber ............ A61B 17/320725 606/159 |
| 7,799,043 | B2 | 9/2010 | O'Brien et al. |
| 7,883,537 | B2 | 2/2011 | Grayzel et al. |
| 7,896,911 | B2 | 3/2011 | Schneider et al. |
| 8,585,959 | B2 | 11/2013 | Burton |
| 2002/0010489 | A1 | 1/2002 | Grayzel et al. |
| 2004/0034384 | A1 | 2/2004 | Fukaya |
| 2005/0149102 | A1 | 7/2005 | Radisch, Jr. et al. |
| 2006/0111736 | A1 | 5/2006 | Kelley |
| 2009/0234283 | A1 | 9/2009 | Burton et al. |
| 2010/0042121 | A1 | 2/2010 | Schneider et al. |

(Continued)

*Primary Examiner* — Victor Nguyen
(74) *Attorney, Agent, or Firm* — Brinks Gilson & Lione

(57) ABSTRACT

A balloon catheter is provided for dilating hardened stenoses. The balloon catheter has dilation elements integrally formed on the outer surface of the balloon. The dilation elements have cross-sectional shapes that improve the performance of the balloon catheter.

14 Claims, 6 Drawing Sheets

(56) References Cited

U.S. PATENT DOCUMENTS

2010/0286593 A1 11/2010 Krolik et al.
2011/0004237 A1* 1/2011 Schneider ................ A61F 2/86
  606/194
2011/0264193 A1 10/2011 Abunassar

* cited by examiner

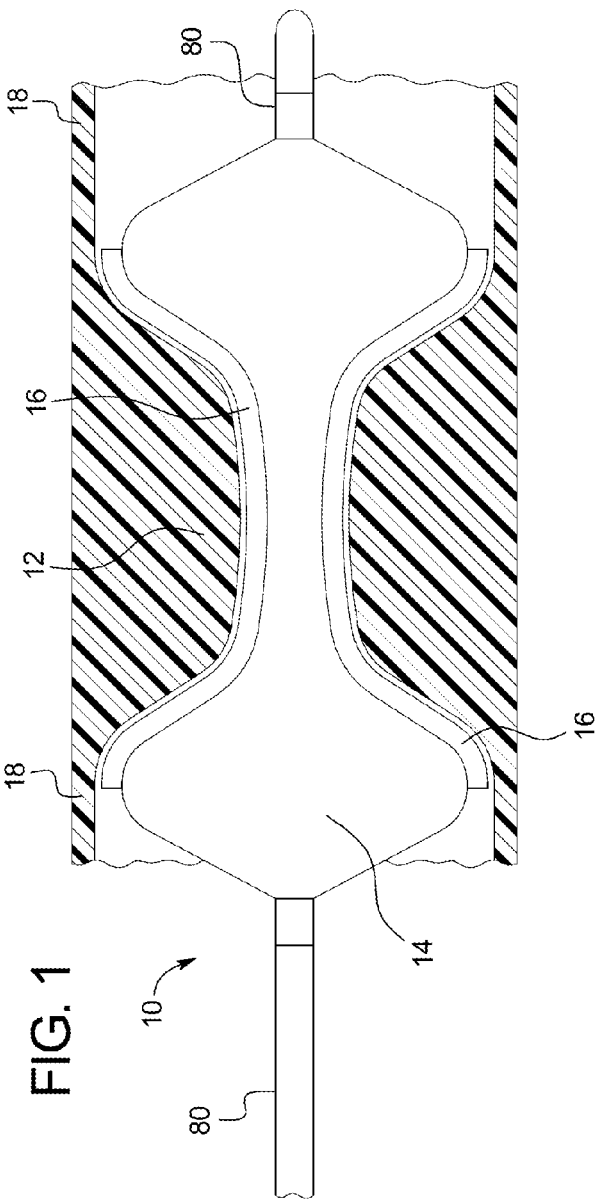
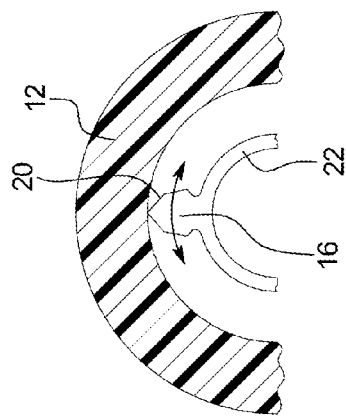
FIG. 1
FIG. 2

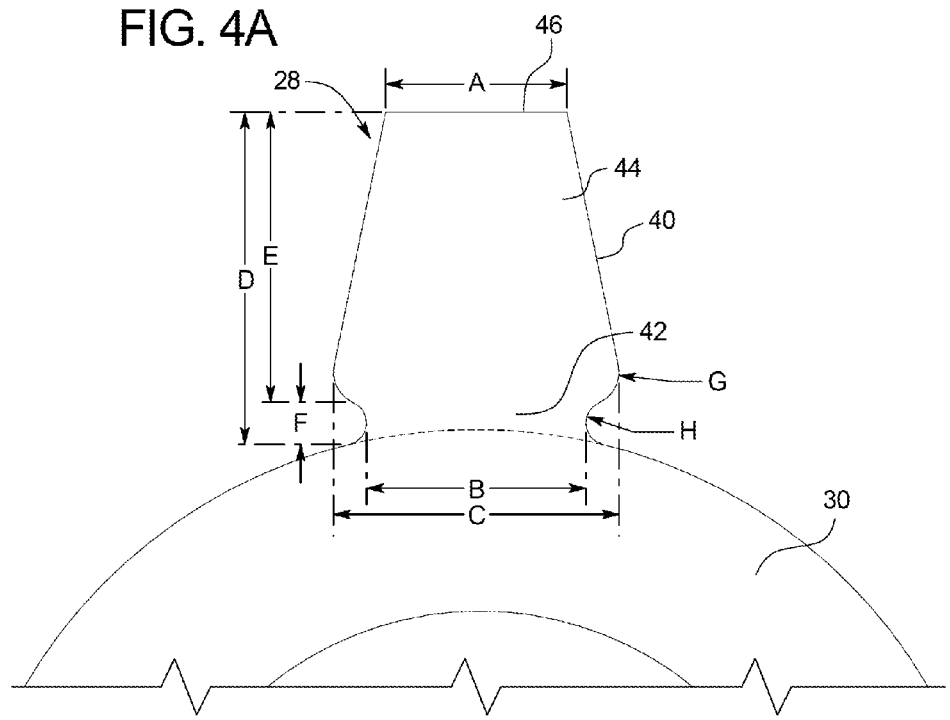
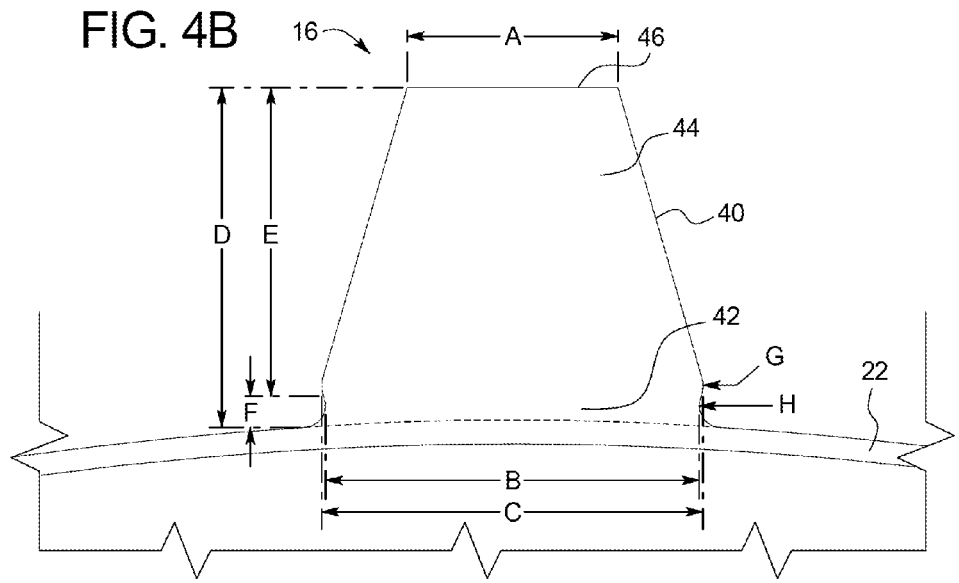

INTEGRAL DILATION ELEMENT FOR A BALLOON CATHETER

This application is a continuation of U.S. patent application Ser. No. 13/690,507, filed Nov. 30, 2012, which claims the benefit under 35 U.S.C. § 119(e) of U.S. Provisional Application No. 61/566,232, filed Dec. 2, 2011, the contents of which applications are hereby incorporated by reference.

BACKGROUND

The present invention relates generally to medical devices and particularly to a balloon catheter with dilation elements on the surface of the balloon.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, vascular angioplasty using a balloon catheter has drawn particular attention from the medical community because of the growing number of people suffering from vascular problems associated with arterial stenosis. This has lead to an increased demand for medical procedures to treat such problems. The widespread frequency of vascular problems may be due to a number of societal changes, including the tendency of people to exercise less while eating greater quantities of unhealthy foods, in conjunction with the fact that people generally now have longer life spans than previous generations. Angioplasty procedures have become a popular alternative for treating arterial stenosis because angioplasty procedures are considerably less invasive than other alternatives. As an example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for vascular treatments, the medical community has turned to angioplasty procedures, in combination with stenting and other procedures, to avoid the problems associated with traditional open surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg or arm arteries) and threading the catheter to the narrowed part of the artery to be treated. During this stage, the balloon is uninflated and collapsed onto the shaft of the catheter in order to present a low profile which may be passed through the vasculature. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. Alternatively, if the balloon catheter is not adapted for delivery of a stent, either a balloon-expandable stent or a self-expandable stent may be implanted in the dilated region in a follow-up procedure. Although the treatment of stenosed arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. One solution that has been offered for dilating hardened stenoses is special balloon catheters with dilation wires or beads that extend along the length of the balloon. The dilation wires and/or beads focus that dilation pressure of the balloon onto the narrower contact area between the dilation wire or bead and the vessel wall. As a result, the increased, focused pressure may crack and/or break up the hardened stenosis, thereby allowing the vessel lumen to be expanded.

One approach that has been used to attach dilation wires and/or beads to a balloon is securing the wires and/or beads to the exterior surface of the balloon with adhesives. However, the use of adhesives to secure dilation wires and/or beads has several disadvantages. For example, there may be concern that the adhesive could detach from the balloon surface and allow the dilation wire and/or bead to break loose. This may be a particular concern when the adhesive is the only or the primary mechanism for securing the dilation wire and/or bead to the balloon surface. Detachment of the adhesive from the balloon surface can be a more serious problem when the balloon is made of a compliant or semi-compliant material, because the balloon material stretches as the balloon expands but the dilation wire and/or bead may not stretch during expansion or may stretch at a different rate. Because of these opposing forces between the balloon material and the dilation wire and/or bead, the adhesive may crack or lose its adherence to the balloon surface. Moreover, even in the case of non-compliant balloons, detachment of the adhesive may be a concern because physicians are particularly adverse to any possible risk of intravascular device failures. The use of adhesives in a manufacturing setting is also disadvantageous. Applying adhesives during the manufacturing process is typically a manually intensive task and time consuming. Maintaining cleanliness standards is also more difficult with the presence of adhesives, since adhesives are generally messy. The use of adhesives also requires extra fixturing to temporarily secure the parts being adhered while the adhesive cures.

One solution to the problem of attaching separate dilation wires and/or beads to the surface of a balloon is to make the dilation element an integral structure with the balloon wall. However, a disadvantage with this approach is that typical materials used to make angioplasty balloons are required to have a certain amount of flexibility and/or elasticity in order to enable formation of the balloon in manufacturing and to perform in the desired fashion in medical procedures. For example, thermoplastic materials are often used to make angioplasty balloons due to their formability properties and their suitability in medical procedures. However, unlike separate dilation elements that can be made from a hard metal and adhered to the balloon surface, integral dilation elements are limited by the material properties of the balloon material. Although an integral dilation element may be co-extruded using a different material that is harder than the material used for the balloon wall, such co-extruded dilation elements are still limited to using materials that are compatible with the material of the balloon wall. Moreover, where the material of the dilation element is the same as the material of the balloon wall, the properties of the dilation element are further limited. Thus, integral dilation elements are typically less capable of dilating hardened stenoses than a comparable separate dilation element made from hard metal.

Accordingly, the inventors believe it would be desirable to provide a balloon catheter with an improved integral dilation element.

SUMMARY

A balloon catheter is described with dilation elements for dilating hardened stenosed regions. The dilation elements may be made from the same material as the balloon wall and are integral with the balloon wall. The dilation elements may have cross-sectional shapes, such as a trizoid shape, trapezoid shape or triangle shape, that improve the performance of the balloon catheter. The inventions herein may also include any other aspect described below in the written description or in the attached drawings and any combinations thereof.

BRIEF DESCRIPTION OF SEVERAL VIEWS OF THE DRAWINGS

The invention may be more fully understood by reading the following description in conjunction with the drawings, in which:

FIG. 1 is a cross-sectional side view of a balloon catheter pressurized within a hardened stenosis;

FIG. 2 is a cross-sectional end view of the balloon catheter pressurized within a hardened stenosis;

FIG. 4A is an enlarged cross-sectional view of a trapezoid-shaped protrusion;

FIG. 4B is an enlarged cross-sectional view of trapezoid-shaped dilation element for a finished balloon;

DETAILED DESCRIPTION

Figure 3A:
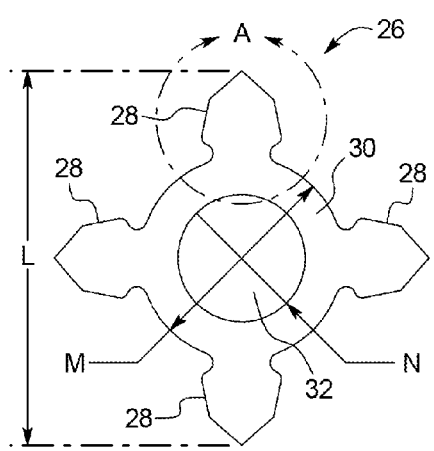
FIG. 3A is a cross-sectional view of a parison with an integral trizoid-shaped protrusion attached to an outer surface thereof.

Referring now to the figures, and particularly to FIG. 1, a balloon catheter 10 is shown inflated within a stenosed artery 12. As shown, the balloon 14 is typically sized to be slightly longer than the stenosed region 12 to ensure that the full length of the stenosis 12 is dilated by the balloon 14. However, a conventional balloon may not be able to dilate a hardened stenosis 12 with conventional balloon pressures. Thus, where the stenosed region 12 is hardened, it may be preferable to use a balloon 14 with integral dilation elements 16 to focus the balloon pressure onto a narrow portion of the stenosis 12, and thereby crack the hardened stenosis 12 in order to dilate it. Preferably, the balloon 14 and integral dilation elements 16 are made from a material with an elastic modulus in the range of about 1,000 MPa to about 2,000 MPa. For example, various polyamides may be suitable, with nylon 12 being one possible material. Preferably, the overall height of each dilation element 16 is about 1.25 mm or less. The dilation elements 16 preferably taper from a wider bottom portion to a narrower top portion, and the widest bottom portion is preferably 1.35 mm or less. Where the dilation elements 16 have a pointed tip 38, 54, it is preferred that the tip 38, 54 have a radius of 0.05 mm or less. In addition, although the dilation elements 16 may extend along only a portion of the length of the balloon 14 and/or the working length, it is preferred that the dilation elements 16 extend along the entire working length of the balloon 14.

As shown in FIG. 1, as the balloon 14 is inflated, the balloon 14 and the dilation elements 16 initially follow the shape of the stenosis 12 and vessel wall 18. Thus, the dilation elements 16 are longitudinally bent around the initial shape of the stenosis 12. As the pressure is increased in the balloon 14, the dilation elements 16 will begin to crack the hardened stenosis 12 and the balloon 14 will dilate the stenosis 12. As a result, the dilation elements 16 will eventually straighten from the initial bent configuration shown in FIG. 1. As shown in FIG. 2, as the dilation elements 16 contact the stenosis 12, the balloon 14 force will be concentrated at the tip 20 of each dilation element 16, which will promote cracking of the stenosis 12 where the tip 20 of the dilation element 16 contacts the stenosis 12. However, the dilation elements 16 may be subjected to a torsional load between the balloon wall 22 and the stenosis 12, which could cause the tip 20 of the dilation element 16 to twist away from the stenosis 12. If this occurs, the dilation element 16 is likely to be less effective at cracking the hardened stenosis 12.

The inventors have discovered that the effectiveness of the dilation elements 16 can be improved by designing a cross-sectional shape that has an area moment of inertia and a polar moment of inertia that are within specific ranges. The area moment of inertia generally relates to the resistance of a beam having a particular cross-sectional shape to bend along the length of the beam. Accordingly, a beam made from a cross-sectional shape with a higher area moment of inertia is more resistant to bending than a beam with a cross-sectional shape with a lower area moment of inertia. For example, an I-beam has a relatively high area moment of inertia and is more resistant to bending than a thin wide beam. The polar moment of inertia generally relates to the resistance of a cross-sectional shape to twist. Accordingly, a beam made from a cross-sectional shape with a higher polar moment of inertia is more resistant to torsional loads than a beam with a cross-sectional shape with a lower polar moment of inertia. For example, although an I-beam is relatively resistant to bending, it is less resistant to torsion, and while a thin wide beam has little resistance to bending, it has more resistance to torsion.

In the design of a balloon catheter 10 with an integral dilation element 16, the area moment of inertia and the polar moment of inertia are both crucial to designing an improved dilation element 16. However, the area moment of inertia and the polar moment of inertia tend to counterbalance each other, and it is not readily apparent what combination of the area moment of inertia and polar moment of inertia will be desirable. In general, it is desirable for the dilation element 16 to resist both bending and torsion. In addition, it is important for the balloon 14 with integral dilation elements 16 to have good folding characteristics so that the balloon 14 presents a low profile in the deflated state. As shown in FIG. 1, the dilation element 16 is subjected to bending loads as the stenosis 12 is dilated. Thus, the resistance of the dilation element 16 to this bending load can help to focus pressure on the stenosis 12 and increase cracking of the stenosis 12. For example, it has been found by the inventors in testing that when the balloon 14 is pressurized within a narrow hollow test piece, the test piece typically cracks first at the end where the dilation elements 16 are subject to the most bending. However, as shown in FIG. 2, the dilation element 16 is also subjected to torsional loads as the stenosis 12 is dilated. Here, it is desirable for the dilation element 16 to have sufficient resistance to the torsional load so that the dilation element 16 remains oriented outward toward the stenosis 12 and does not twist sideways away from the stenosis 12.

Figure 3B:
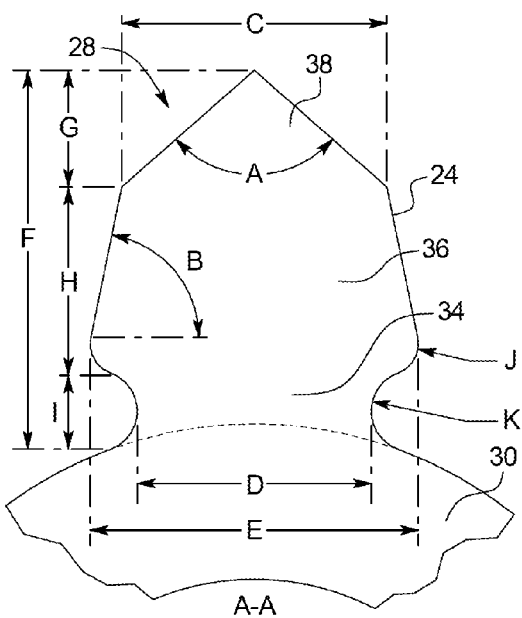
FIG. 3B is an enlarged cross-sectional view of the protrusion of FIG. 3A.
Figure 3C:
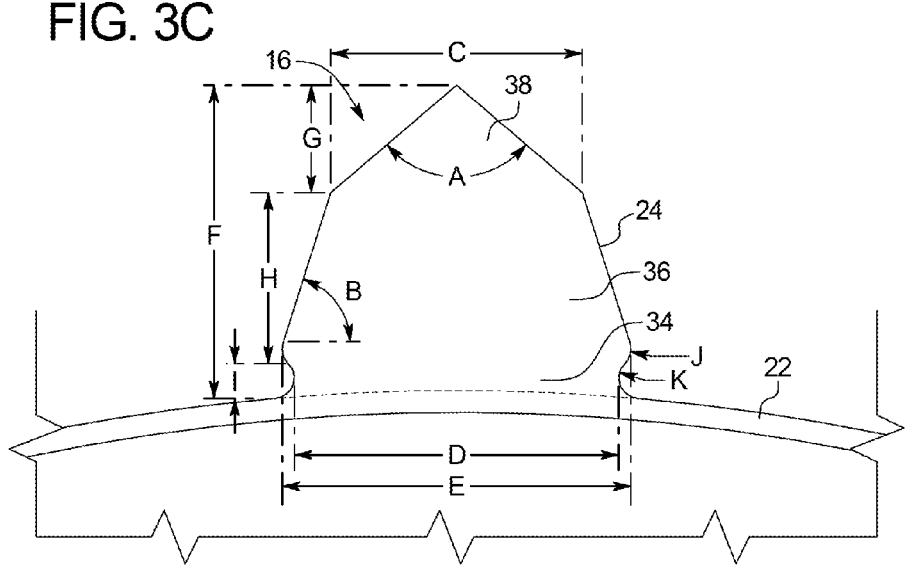
FIG. 3C is an enlarged cross-sectional view of trizoid-shaped dilation element for a finished balloon.

Turning to FIGS. 3A-3C, one effective shape for an integral dilation element 16 may be a trizoid cross-sectional shape 24. The dilation element 16 is integrally attached to the wall 32 of the balloon 14. The final cross-sectional shape of the dilation element 16 on the finished balloon is shown in FIG. 3C. In FIG. 3A, a tube 26, or parison 26, is shown that is used to form the balloon 14 and finished dilation element 16. In FIG. 3B, one of the protrusions 28 attached to the tube 26 of FIG. 3A is shown in more detail. As described below, the protrusions 28 and tube 26 are formed during manufacturing into the finished dilation elements 16 and balloon 14, respectively.

As shown in FIG. 3A, the tube 26 has a generally circular wall 30 surrounding a central lumen 32. As will be understood from the description below, the central lumen 32 will form the interior cavity of the finished balloon 14, with the circular wall 30 forming the balloon wall 22. A series of protrusions 28 are integrally attached to the outer surface of the circular wall 30 and extend along the length of the tube 26.

As shown in FIG. 3B, the protrusion 28 has a neck 34 that integrally connects the protrusion 28 to the wall 30. A body portion 36 is connected to the neck 34. The bottom portion of the body portion 36 is preferably wider than the neck 34, and the body portion 36 is preferably tapered so that the top portion of the body portion 36 is narrower than the bottom portion. A tip 38 is connected to the top portion of the body portion 36. The tip 38 is preferably more tapered than the body portion 36 and is preferably pointed.

As described further below, the tube 26 with protrusions 28 is expanded inside of a mold by heating the tube 26 and pressurizing the central lumen 32. During this process the tube wall 30 thins out to form the finished balloon wall 22, and the protrusions 28 change shape slightly to form the finished dilation elements 16. However, during the forming process, the features of the cross-sectional shape 24 generally stay the same, and only the dimensions of the cross-sectional shape 24 change. Representative dimensions for the trizoid cross-sectional shape 24 are shown below in Table 1. Although it is possible for the pointed tip 38 to be radiused, it is preferred for the trizoid cross-sectional shape 24 to have a pointed tip 38 that is generally sharp. It is also preferable for the bottom width of the tip 38 to be about 1.0 mm to about 0.25 mm. Preferably, the area moment of inertia of the finished dilation elements 16 is within a range of about 0.200 mm$^4$ to about 0.0005 mm$^4$. A more preferred range for the area moment of inertia is about 0.005 mm$^4$ to about 0.0005 mm$^4$. The most preferred value for the area moment of inertia is about 0.0017 mm$^4$. Preferably, the polar moment of inertia of the finished dilation elements 16 is within a range of about 0.44 mm$^4$ to about 0.001 mm$^4$. A more preferred range for the polar of inertia is about 0.010 mm$^4$ to about 0.001 mm$^4$. The most preferred value for the polar moment of inertia is about 0.0035 mm$^4$.

TABLE 1

Trizoid Dilation Element

| | | 5 mm Balloon | | 8 mm Balloon | | 12 mm Balloon | |
|---|---|---|---|---|---|---|---|
| Description | Ref. | Tube FIG. 3B | Final FIG. 3C | Tube FIG. 3B | Final FIG. 3C | Tube FIG. 3B | Final FIG. 3C |
| Angle of Tip | A | 96.919° | 98.880° | 93.536° | 95.520° | 93.536° | 95.520° |
| Angle of Body Portion | B | 79.084° | 72.610° | 79.122° | 73.040° | 79.120° | 73.040° |
| Width of Tip | C | 0.4750 | 0.2900 | 0.5160 | 0.3150 | 0.5160 | 0.3150 |
| Width of Neck | D | 0.4130 | 0.3720 | 0.4540 | 0.4090 | 0.4540 | 0.4090 |
| Width of Body Portion | E | 0.5800 | 0.4000 | 0.6380 | 0.4400 | 0.6380 | 0.4400 |
| Overall Height | F | 0.6754 | 0.3610 | 0.7656 | 0.4100 | 0.7656 | 0.4100 |
| Height of Tip | G | 0.2104 | 0.1240 | 0.2426 | 0.1430 | 0.2426 | 0.1430 |
| Height of Body Portion | H | 0.3340 | 0.1970 | 0.3850 | 0.2270 | 0.3850 | 0.2270 |
| Height of Neck | I | 0.1310 | 0.0400 | 0.1380 | 0.0400 | 0.1380 | 0.0400 |
| Bottom Radius of Body Portion | J | 0.0600 | 0.0250 | 0.0650 | 0.0250 | 0.0650 | 0.0250 |
| Radius of Neck | K | 0.0698 | 0.0240 | 0.0721 | 0.0230 | 0.0715 | 0.0230 |
| Length from Tip to Tip | L | 2.7631 | 5.72 | 3.7303 | 8.82 | 4.7811 | 12.82 |
| Outer Diameter of Wall | M | 1.5000 | 5.00 | 2.2700 | 8.00 | 3.3000 | 12.00 |
| Inner Diameter of Wall | N | 0.9400 | 4.90 | 1.4800 | 7.88 | 2.2600 | 11.84 |
| Area Moment of Inertia | | 0.0067 | 0.00066 | 0.01035 | 0.0014 | 0.1035 | 0.0014 |
| Polar Moment of Inertia | | 0.0134 | 0.00132 | 0.0207 | 0.0028 | 0.0207 | 0.0028 |

Turning to FIGS. 4A-4B, another effective shape for an integral dilation element 16 may be a trapezoid cross-sectional shape 40. The final cross-sectional shape of the dilation element 16 on the finished balloon 14 is shown in FIG. 4B. The initial cross-sectional shape of the protrusion 28 before forming the balloon 14 is shown in FIG. 4A. As shown in FIGS. 4A-4B, the protrusion 28 and dilation element 16 have a neck 42 that integrally connects the protrusion 28 and dilation element 16 to the wall 30, 22. A body portion 44 is connected to the neck 42. The bottom portion of the body portion 44 is preferably wider than the neck 42, and the body portion 44 is preferably tapered so that the top portion of the body portion 44 is narrower than the bottom portion. The tip 46 of the protrusion 28 and dilation element 16 is preferably flat. Representative dimensions for the trapezoid cross-sectional shape 40 are shown below in Table 2. Preferably, the area moment of inertia of the finished dilation elements 16 is within a range of about 0.125 mm$^4$ to about 0.0005 mm$^4$. A more preferred range for the area moment of inertia is about 0.0025 mm$^4$ to about 0.00095 mm$^4$. The most preferred value for the area moment of inertia is about 0.0017 mm$^4$. Preferably, the polar moment of inertia of the finished dilation elements 16 is within a range of about 0.250 mm$^4$ to about 0.001 mm$^4$. A more preferred range for the polar of inertia is about 0.005 mm$^4$ to about 0.0019 mm$^4$. The most preferred value for the polar moment of inertia is about 0.0034 mm$^4$.

TABLE 2

Trapezoid Dilation Element

| | | 8 mm Balloon | |
| --- | --- | --- | --- |
| | Ref. | Tube FIG. 4A | Final FIG. 4B |
| Top Width of Body Portion | A | 0.3950 | 0.2400 |
| Width of Neck | B | 0.4740 | 0.4200 |
| Bottom Width of Body Portion | C | 0.6210 | 0.4300 |
| Overall Height | D | 0.7210 | 0.3850 |
| Height of Body Portion | E | 0.6310 | 0.3500 |
| Height of Neck | F | 0.0900 | 0.0350 |
| Bottom Radius of Body Portion | G | 0.0720 | 0.0300 |
| Radius of Neck | H | 0.0480 | 0.0250 |
| Length from Tip to Tip | | 3.62 | 8.77 |
| | | 2.26 | 2.26 |
| | | 0.010 | 8.00 |
| | | | 1.48 | 
| | | | 7.88 |
| Area Moment of Inertia | | 0.010 | 0.00143 |
| Polar Moment of Inertia | | 0.0198 | 0.00287 |

Figure 5A:
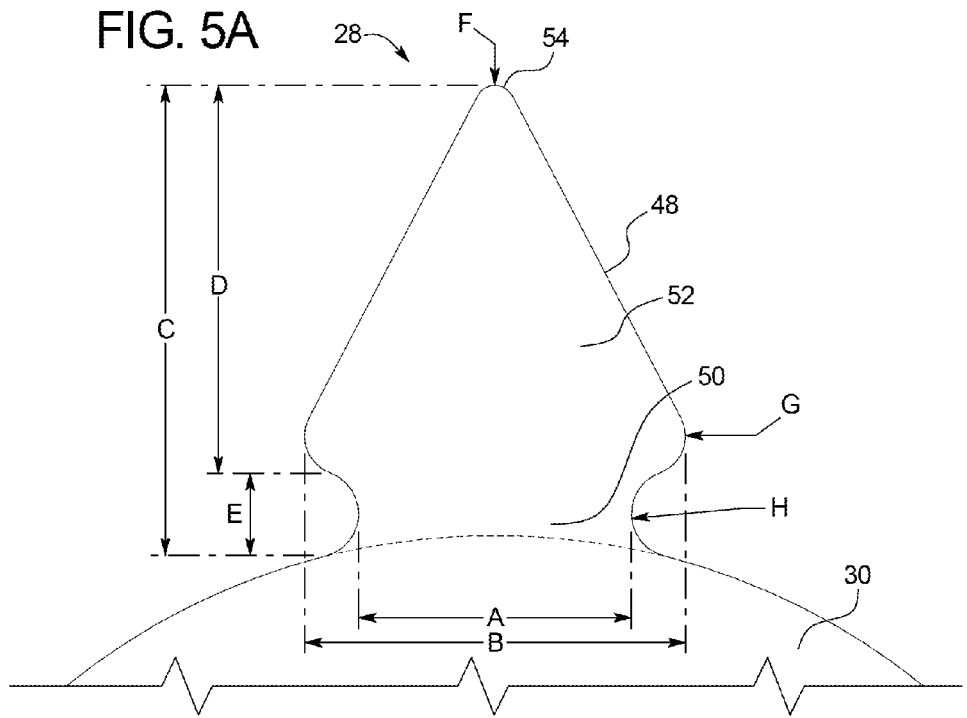
FIG. 5A is an enlarged cross-sectional view of a triangle-shaped protrusion.
Figure 5B:
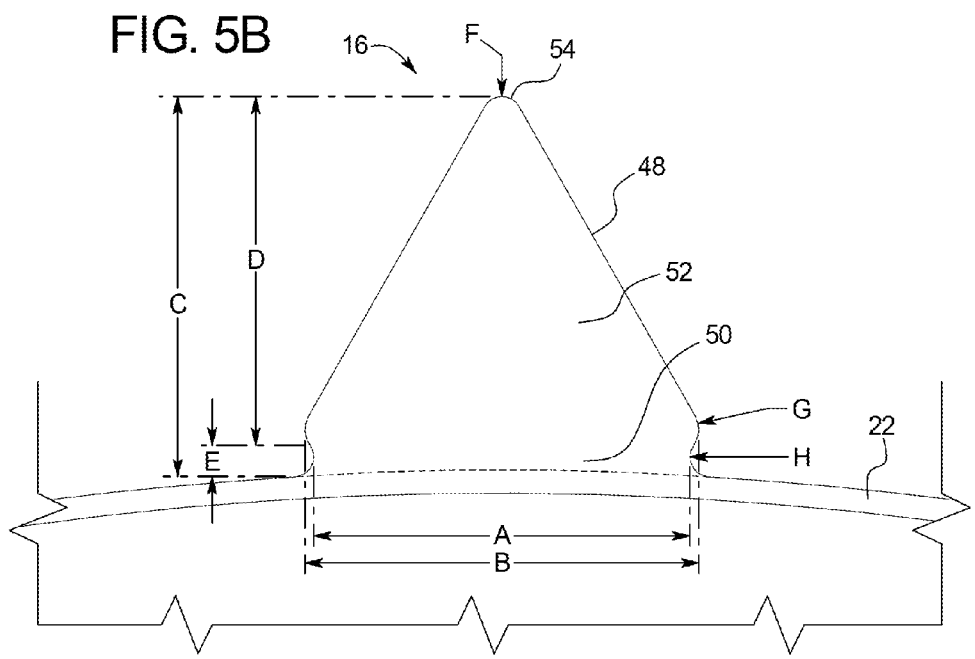
FIG. 5B is an enlarged cross-sectional view of triangle-shaped dilation element for a finished balloon.

Turning FIGS. 5A-5B, another effective shape for an integral dilation element 16 may be a triangle cross-sectional shape 48. The final cross-sectional shape of the dilation element 16 on the finished balloon 14 is shown in FIG. 5B. The initial cross-sectional shape of the protrusion 28 before forming the balloon 14 is shown in FIG. 5A. As shown in FIGS. 5A-5B, the protrusion 28 and dilation element 16 have a neck 50 that integrally connects the protrusion 28 and dilation element 16 to the wall 30, 22. A body portion 52 is connected to the neck 50. The bottom portion of the body portion 52 is preferably wider than the neck 50, and the body portion 52 is preferably tapered to a pointed tip 54. Representative dimensions for the triangle cross-sectional shape 48 are shown below in Table 3. Although it is possible for the pointed tip 54 to be sharp, it is preferred for the triangle cross-sectional shape 48 to have a pointed tip 54 with a radius of about 0.010 mm to about 0.050 mm. Preferably, the area moment of inertia of the finished dilation elements 16 is within a range of about 0.075 mm$^4$ to about 0.00035 mm$^4$. A more preferred range for the area moment of inertia is about 0.00144 mm$^4$ to about 0.0006 mm$^4$. The most preferred value for the area moment of inertia is about 0.00125 mm$^4$. Preferably, the polar moment of inertia of the finished dilation elements 16 is within a range of about 0.150 mm$^4$ to about 0.00068 mm$^4$. A more preferred range for the polar of inertia is about 0.00288 mm$^4$ to about 0.0012 mm$^4$. The most preferred value for the polar moment of inertia is about 0.0025 mm$^4$.

TABLE 3

Triangle Dilation Element

| | | 8 mm Balloon | |
| --- | --- | --- | --- |
| | Ref. | Tube FIG. 5A | Final FIG. 5B |
| Width of Neck | A | 0.4540 | 0.4200 |
| Bottom Width of Body Portion | B | 0.6380 | 0.4400 |
| Overall Height | C | 0.7820 | 0.4230 |
| Height of Body Portion | D | 0.6440 | 0.3880 |
| Height of Neck | E | 0.1380 | 0.0350 |
| Radius of Tip | F | 0.0350 | 0.0230 |
| Bottom Radius of Body Portion | G | 0.0650 | 0.0300 |
| Radius of Neck | H | 0.0720 | 0.0220 |
| Length from Tip to Tip | | 3.74 | 8.85 |
| Outer Diameter of Wall | | 2.26 | 8.00 |
| Inner Diameter of Wall | | 1.48 | 7.88 |
| Area Moment of Inertia | | 0.0735 | 0.00115 |
| Polar Moment of Inertia | | 0.147 | 0.00231 |

Turning now to the method of manufacturing the balloon catheter 10, the tube 26 may be continuously extruded through a mold from a polymer material. Thus, each of the structures of the extruded tube 26 are integral with each other and extend along the entire length of the extruded tube 26. Although the tube 26 may be co-extruded with different materials for the protrusion 28 and the wall 30 that are compatible with each other, it is preferable for the protrusion 28 and wall 30 to be formed from the same material. The extruded tube 26 may have a central lumen 32 that is used for blow molding the tube 26 as described below. The central lumen 32 will form the inner lumens of the neck regions 78, which are attached to a catheter 80, and will also form the interior cavity of the balloon 14, which allows the balloon 14 to expand from a deflated state to an expanded state.

The extruded tube 26 also includes a protrusion 28 on the outer surface that extends longitudinally along the length of the extruded tube 26. The cross-sectional shape of the protrusion 28 may be any shape suitable for a particular application and may be one of the cross-sectional shapes 24, 40, 48 described above. Preferably, the protrusion 28 is defined by an area moment of inertia of about 0.70 mm$^4$ to about 0.0035 mm$^4$ and a polar moment of inertia of about 0.35 mm$^4$ to about 0.007 mm$^4$. After the protrusion 28 is formed into the final dilation element 16, the area moment of inertia preferably changes to about 0.0875 mm$^4$ to about 0.00045 mm$^4$, and the polar moment of inertia changes to about 0.175 mm$^4$ to about 0.0009 mm$^4$. More preferably, the protrusion 28 is defined by an area moment of inertia of about 0.0635 mm$^4$ to about 0.006 mm$^4$ and a polar moment of inertia of about 0.127 mm$^4$ to about 0.012 mm$^4$. After the protrusion 28 is formed into the final dilation element 16, the area moment of inertia more preferably changes to about 0.0083 mm$^4$ to about 0.0008 mm$^4$, and the polar moment of inertia changes to about 0.0166 mm$^4$ to about 0.0016 mm$^4$. Most preferably, the protrusion 28 is defined by an area moment of inertia of about 0.024 mm$^4$ to about 0.006 mm$^4$ and a polar moment of inertia of about 0.048 mm$^4$ to about 0.012 mm$^4$. After the protrusion 28 is formed into the final dilation element 16, the area moment of inertia most preferably changes to about 0.003125 mm$^4$ to about 0.0008 mm$^4$, and the polar moment of inertia changes to about 0.00625 mm$^4$ to about 0.0016 mm$^4$.

Figure 6:
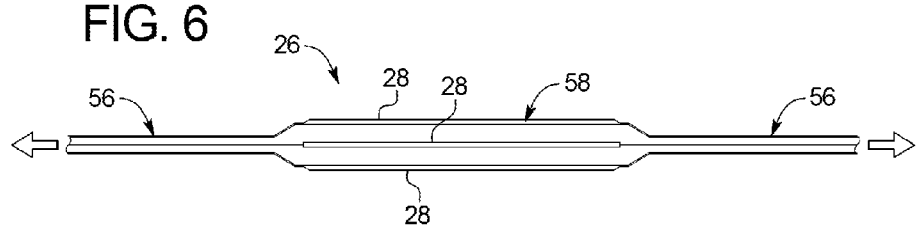
FIG. 6 is a side view of a tube being stretched.

As shown in FIG. 6, it may be preferable to initially stretch a portion 56 of the tube 26. The initial stretching process may be achieved by heating one end 56 of the tube 26 without heating the middle 58 of the tube 26. The heated end 56 of the tube 26 may be pulled to stretch it without causing the middle portion 58 to be stretched. The other end 56 may then be heated and stretched in a similar manner. The initial stretching step may be helpful to define the region of the balloon 14 that will form the expanded balloon 14 after blow molding.

Figure 7:
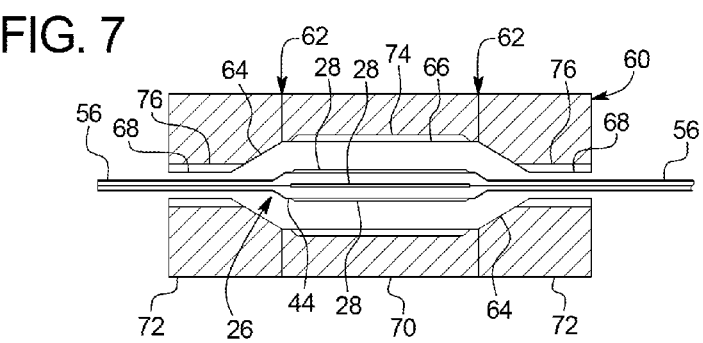
FIG. 7 is a side view of the tube in a mold.

As shown in FIG. 7, the tube 26 may then be positioned within a mold 60 for blow molding. While the mold 60 may take various forms, a three-piece mold 60 may be desirable. The three-piece mold 60 may be split in two places 62 at the transition between the tapered regions 64 and the working diameter 66. The tube 26 may be inserted into the mold 60 by separating one or more of the pieces of the mold 60 and inserting one end 56 of the tube 26 through one of the neck regions 68 n the mold 60. The working diameter piece 70 and/or the other neck piece 72 may then be slid over the other end 56 of the tube 26.

Figure 8:
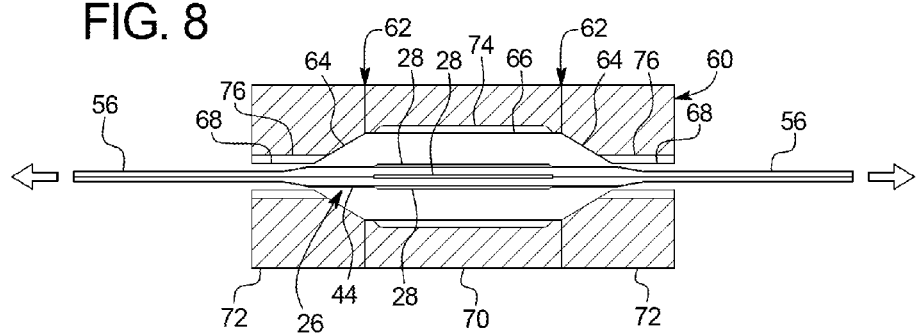
FIG. 8 is a side view of the tube in the mold and being stretched.

As shown in FIG. 8, the tube 26 is preferably heated and stretched in the mold 60 prior to blow molding. A small amount of pressure may be applied to the central lumen 32 during the initial stretching, but preferably, the central lumen pressure does not cause substantial dimensional changes to the tube 26. Stretching may be done by heating at least the middle portion 58 of the tube 26 and pulling on the ends 56 of the tube 26. Although a larger portion of the tube 26 may be heated, it may be desirable to only heat the portion of the tube 26 where the dilation elements 16 will be formed and a small length beyond the ends of the dilation elements 16.

Figure 9:
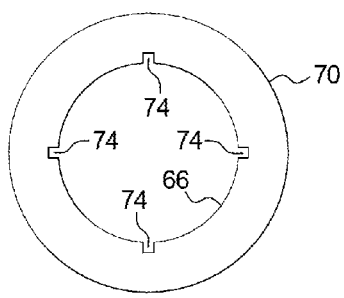
FIG. 9 is an end view of a working diameter piece of the mold.

As shown in FIG. 9, the mold 60 may also have longitudinal clearance cavities 74 along the working diameter 66 that receive the protrusions 28. If desired, the working diameter clearance cavity 74 may be sized so that the protrusion 28 does not significantly contact the mold 60 during blow molding to avoid changing the shape of the protrusion 28. Alternatively, the working diameter clearance cavity 74 can be sized to contact the protrusion 28 during blow molding to cause the protrusion 28 to be reformed into the final desired shape during blow molding. Preferably, the tapered regions 64 of the mold 60 do not have any clearance cavities to receive the protrusion 28. As a result, when the tube 26 is blow molded, the protrusions 28 are compressed against the tapered regions 64 of the mold 60 and are either mostly or entirely reformed into the wall of the finished balloon 14. Similarly, the clearance cavities 74 along the working diameter 66 may be omitted near the ends of the working diameter 66 to compress the protrusions 28 adjacent the ends of the dilation elements 16. The neck regions 68 of the mold 60 may or may not have clearance cavities for the protrusion 28. However, it may be desirable to provide clearance cavities 76 that partially receive the protrusions 28 in order to index and align the tube 26 to the mold 60. The neck region clearance cavities 76 may be sized so that they partially reshape the protrusions 28 during blow molding to partially reform the protrusions 28 into the neck regions 78 of the balloon 14. Once the tube 26 has been indexed to the mold 60 so that the protrusions 28 are aligned with the clearance cavities 74, 76, the tube 26 is blow molded in the mold 60 by heating the tube 26 and pressurizing the central opening 32. This causes the tube 26 to circumferentially stretch and expand outward against the walls of the mold 60. If it is desirable to minimize reforming and stretching of the protrusions 28 during blow molding, narrowed necks 34 as described above may be used to isolate the protrusions 28 from the wall 30 of the tube 26 during blow molding.

Figure 10:
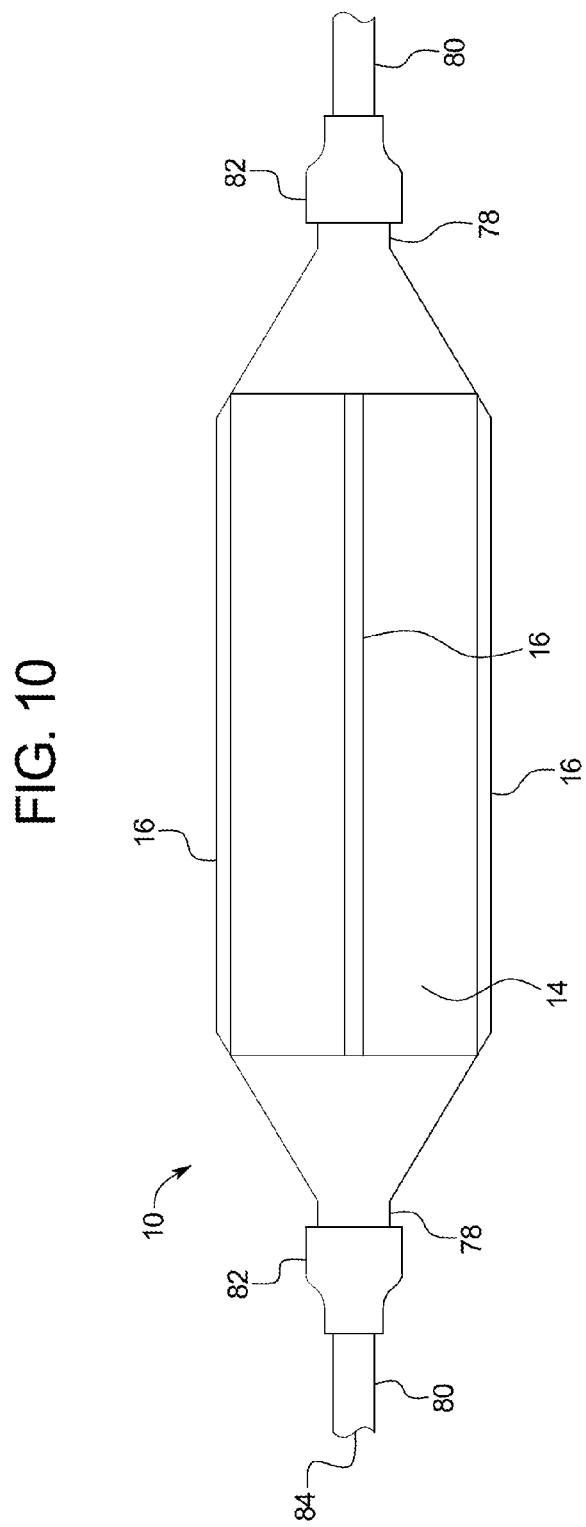
FIG. 10 is a side view of a balloon catheter with the dilation elements.

As shown in FIG. 10, after the tube 26 has been blow molded, the balloon 14 is cooled and removed from the mold 60. The balloon 14 is then mounted onto a catheter 80 by inserting the catheter 80 through the inner lumens of the neck regions 78 of the balloon 14. Preferably, the catheter 80 is bonded and sealed to the neck regions 78 of the catheter 80 by melt bonding. This may be accomplished by disposing heat shrink tubing 82 over the neck regions 78 of the balloon 14. The heat shrink tubing 82, neck regions 78 and catheter 80 are then heated. The heat softens the neck regions 78 and the catheter 80 and causes the heat shrink tubing 82 to shrink and squeeze the neck regions 78 and catheter 80 together. As a result, the neck regions 78 and catheter 80 melt together and adhere to each other when the heat shrink tubing 82, neck regions 78 and catheter 80 cool. In addition, the protrusions 28 are substantially reformed into the exterior surface of the neck regions 78 of the balloon 14 by the pressure of the heat shrink tubing 82 and the softening caused by the heat. This provides a smooth attachment between the catheter 80 and the balloon 14 without any significant remnant of the protrusions 28 in the neck regions 78.

Thus as shown in FIG. 10, the final balloon catheter 10 has a balloon 14 mounted on the distal end of the catheter shaft 80. Integral dilation elements 16 are formed on the outer surface of the balloon 14 and extend along the length of the working diameter of the balloon 14. The catheter shaft 80 has an inflation lumen 84 extending longitudinally through the catheter shaft 80 which is in communication with the interior cavity of the balloon 14 to inflate and deflate the balloon 14 with inflation media. As described above, the cross-sectional shapes 24, 40, 48 of the dilation elements 16 are particularly well-suited for dilating hardened stenosed regions.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A method of manufacturing a balloon catheter, comprising:
    placing a tube inside a mold, said tube comprising a generally circular wall surrounding a central lumen and a protrusion integrally attached to an outer surface of said generally circular wall and extending along a length thereof;
    expanding a portion of said tube inside of the mold by heating said tube and pressurizing said central lumen, said mold comprising a longitudinal clearance cavity to receive a length of said protrusion, said tube forming a balloon and said protrusion forming a dilation element after said expanding, said balloon comprising a central working diameter portion and end neck regions;
    bonding said end neck regions to a catheter shaft, an inflation lumen being in communication with an interior cavity of said balloon to inflate and deflate said balloon.

2. The method according to claim 1, wherein said longitudinal clearance cavity along at least a portion of said working diameter portion is sized so that said protrusion does not significantly contact said mold during said expanding.

3. The method according to claim 2, wherein said longitudinal clearance cavity at least partially receives said protrusion along at least a portion of said neck regions, said longitudinal clearance cavity in said neck regions thereby indexing said tube to said longitudinal clearance cavity along said working diameter portion.

4. The method according to claim 3, wherein said bonding comprises disposing heat shrink tubing over said protrusion along said neck regions after said heating and pressurizing.

5. The method according to claim 4, wherein said disposing comprises applying sufficient heat to said neck region to substantially reform said protrusion into the outer surface of said generally circular wall.

6. The method according to claim 2, wherein a shape of said protrusion does not change shape during said expanding.

7. The method according to claim 1, wherein said mold does not comprise a longitudinal clearance cavity receiving said protrusion along tapered regions extending between said working region and said neck regions, said protrusion thereby being compressed against said mold at said tapered regions.

8. The method according to claim 1, said protrusion comprising a protrusion body portion attaching to said generally circular wall by a protrusion neck portion, wherein a bottom portion of said protrusion body portion is wider than said protrusion neck portion.

9. The method according to claim 1, comprising a plurality of protrusions integrally attached to said outer surface of said generally circular wall.

10. The method of claim 1, wherein said protrusion and said generally circular wall are formed from the same material.

11. The method of claim 10, wherein said protrusion and said generally circular wall are co-extruded.

12. The method of claim 1, wherein bonding said balloon to said catheter shaft comprises inserting said catheter through said central lumen at said neck region and sealing said neck region to said catheter shaft.

13. The method of claim 1, wherein said protrusion is trapezoid-shaped.

14. The method of claim 1, wherein said protrusion is triangle-shaped.

* * * * *